US008639455B2

(12) United States Patent
Horst et al.

(10) Patent No.: US 8,639,455 B2
(45) Date of Patent: Jan. 28, 2014

(54) FOOT PAD DEVICE AND METHOD OF OBTAINING WEIGHT DATA

(75) Inventors: Robert W. Horst, San Jose, CA (US); Robert L. Jardine, Cupertino, CA (US); Jonathan Smith, Waterside (CA); Edith Arnold, San Francisco, CA (US)

(73) Assignee: AlterG, Inc., Fremont, CA (US)

( * ) Notice: Subject to any disclaimer, the term of this patent is extended or adjusted under 35 U.S.C. 154(b) by 1025 days.

(21) Appl. No.: 12/703,067

(22) Filed: Feb. 9, 2010

(65) Prior Publication Data

US 2010/0211355 A1 Aug. 19, 2010

Related U.S. Application Data

(60) Provisional application No. 61/151,103, filed on Feb. 9, 2009.

(51) Int. Cl.
*G01L 5/00* (2006.01)
*G01L 3/00* (2006.01)

(52) U.S. Cl.
USPC .............. 702/44; 702/101; 702/173; 600/592

(58) Field of Classification Search
USPC ............. 702/41, 44, 101, 102, 141, 173, 174; 73/172; 177/245, 264; 600/592
See application file for complete search history.

(56) References Cited

U.S. PATENT DOCUMENTS

| | | | |
|---|---|---|---|
| 1,286,482 A | 12/1918 | Yoder | |
| 1,366,904 A | 2/1921 | Davis | |
| 1,391,290 A | 9/1921 | Welffens | |
| 1,513,473 A | 10/1924 | Ackerman | |
| 1,739,053 A | 12/1929 | Wilhelm | |
| 1,847,720 A | 3/1932 | Marcellis | |
| 2,169,813 A | 8/1939 | Parkin | |
| 3,059,490 A | 10/1962 | McDuffie | |
| 3,200,666 A | 8/1965 | Schrodt et al. | |

(Continued)

FOREIGN PATENT DOCUMENTS

| | | |
|---|---|---|
| EP | 1138286 A2 | 10/2001 |
| EP | 1410780 A1 | 4/2004 |

(Continued)

OTHER PUBLICATIONS

Horst, Robert W.; U.S. Appl. No. 13/290,980 entitled "Intention-based therapy device and method," filed Nov. 7, 2011.

(Continued)

*Primary Examiner* — Manuel L Barbee
(74) *Attorney, Agent, or Firm* — Shay Glenn LLP

(57) ABSTRACT

A foot pad device and a method of obtaining weight data from a force sensor in a foot pad worn by a user engaging in a footstep, including placing the force sensor under the ball of the foot of the user and/or the heel of the foot of the user; receiving an entered patient weight value for the user; collecting force data from the force sensor; calculating a weight value based on the collected force data and a scaling and/or offset parameter; comparing the calculated weight value to the entered patient weight value; comparing the calculated weight value to zero; adjusting the scaling and/or offset parameter; and repeating the steps periodically. The method may include comparing the collected force data to a functionality indication range, flagging the force sensor if the collected force data is outside the functionality indication range, and disregarding force data from the flagged force sensor.

26 Claims, 9 Drawing Sheets

(56) References Cited

U.S. PATENT DOCUMENTS

| | | |
|---|---|---|
| 3,358,678 A | 12/1967 | Kultsar |
| 3,398,248 A | 8/1968 | Klauss et al. |
| 3,402,942 A | 9/1968 | Shimano et al. |
| 3,631,542 A | 1/1972 | Potter |
| 3,641,843 A | 2/1972 | Lemmens |
| 3,863,512 A | 2/1975 | Crawley |
| 3,899,383 A | 8/1975 | Schultz et al. |
| 3,925,131 A | 12/1975 | Krause |
| 3,976,057 A | 8/1976 | Barclay |
| 4,474,176 A | 10/1984 | Farris et al. |
| 4,507,104 A | 3/1985 | Clark et al. |
| 4,538,595 A | 9/1985 | Hajianpour |
| 4,549,555 A | 10/1985 | Fraser et al. |
| 4,588,040 A | 5/1986 | Albright, Jr. et al. |
| 4,649,488 A | 3/1987 | Osanai et al. |
| 4,665,899 A | 5/1987 | Farris et al. |
| 4,678,354 A | 7/1987 | Olsen |
| 4,679,548 A | 7/1987 | Pecheux |
| 4,691,694 A | 9/1987 | Boyd et al. |
| 4,697,808 A | 10/1987 | Larson et al. |
| 4,731,044 A | 3/1988 | Mott |
| 4,745,930 A | 5/1988 | Confer |
| 4,754,185 A | 6/1988 | Gabriel et al. |
| 4,796,631 A | 1/1989 | Grigoryev |
| 4,801,138 A | 1/1989 | Airy et al. |
| 4,807,874 A | 2/1989 | Little |
| 4,872,665 A | 10/1989 | Chareire |
| 4,878,663 A | 11/1989 | Luquette |
| 4,883,445 A | 11/1989 | Gomoll et al. |
| 4,922,925 A | 5/1990 | Crandall et al. |
| 4,934,694 A | 6/1990 | McIntosh |
| 4,944,713 A | 7/1990 | Salerno |
| 4,953,543 A | 9/1990 | Grim et al. |
| 4,981,116 A | 1/1991 | Trinquard |
| 4,983,146 A | 1/1991 | Charles et al. |
| 5,020,790 A | 6/1991 | Beard et al. |
| 5,052,681 A | 10/1991 | Williams |
| 5,078,152 A | 1/1992 | Bond et al. |
| 5,117,814 A | 6/1992 | Luttrell et al. |
| 5,170,776 A | 12/1992 | Pecheux |
| 5,170,777 A | 12/1992 | Reddy et al. |
| 5,195,617 A | 3/1993 | Clemens |
| 5,203,321 A | 4/1993 | Donovan et al. |
| 5,209,223 A | 5/1993 | McGorry et al. |
| 5,213,094 A | 5/1993 | Bonutti |
| 5,239,222 A | 8/1993 | Higuchi et al. |
| 5,241,952 A | 9/1993 | Ortiz |
| 5,282,460 A | 2/1994 | Boldt |
| 5,303,716 A | 4/1994 | Mason et al. |
| 5,313,968 A | 5/1994 | Logan et al. |
| 5,345,834 A | 9/1994 | Hayashi |
| 5,358,468 A | 10/1994 | Longo et al. |
| 5,378,954 A | 1/1995 | Higuchi et al. |
| 5,395,303 A | 3/1995 | Bonutti et al. |
| 5,421,798 A | 6/1995 | Bond et al. |
| 5,440,945 A | 8/1995 | Penn |
| 5,448,124 A | 9/1995 | Higuchi et al. |
| 5,463,526 A | 10/1995 | Mundt |
| 5,476,441 A | 12/1995 | Durfee et al. |
| 5,509,894 A | 4/1996 | Mason et al. |
| 5,520,627 A | 5/1996 | Malewicz |
| 5,525,642 A | 6/1996 | Cipriano et al. |
| 5,534,740 A | 7/1996 | Higuchi et al. |
| 5,541,465 A | 7/1996 | Higuchi et al. |
| 5,573,088 A | 11/1996 | Daniels |
| 5,582,579 A | 12/1996 | Chism et al. |
| 5,585,683 A | 12/1996 | Higuchi et al. |
| 5,608,599 A | 3/1997 | Goldman |
| 5,624,390 A | 4/1997 | Van Dyne |
| 5,653,680 A | 8/1997 | Cruz |
| 5,662,594 A | 9/1997 | Rosenblatt |
| 5,662,693 A | 9/1997 | Johnson et al. |
| 5,674,262 A | 10/1997 | Tumey |
| 5,683,351 A | 11/1997 | Kaiser et al. |
| 5,704,440 A | 1/1998 | Urban et al. |
| 5,708,319 A | 1/1998 | Ban et al. |
| 5,728,017 A | 3/1998 | Bellio et al. |
| 5,746,684 A | 5/1998 | Jordan |
| 5,746,704 A | 5/1998 | Schenck et al. |
| 5,755,303 A | 5/1998 | Yamamoto et al. |
| 5,789,843 A | 8/1998 | Higuchi et al. |
| 5,833,257 A | 11/1998 | Kohlheb et al. |
| 5,865,770 A | 2/1999 | Schectman |
| 5,916,689 A | 6/1999 | Collins et al. |
| 5,931,756 A | 8/1999 | Ohsono et al. |
| 5,976,063 A | 11/1999 | Joutras et al. |
| 6,001,075 A | 12/1999 | Clemens et al. |
| 6,033,330 A | 3/2000 | Wong et al. |
| 6,062,096 A | 5/2000 | Lester |
| 6,119,539 A | 9/2000 | Papanicolaou |
| 6,146,341 A | 11/2000 | Sato et al. |
| 6,149,612 A | 11/2000 | Schnapp et al. |
| 6,162,189 A | 12/2000 | Girone et al. |
| 6,183,431 B1 | 2/2001 | Gach, Jr. |
| 6,217,532 B1 | 4/2001 | Blanchard et al. |
| 6,221,032 B1 | 4/2001 | Blanchard et al. |
| 6,290,662 B1 | 9/2001 | Morris et al. |
| 6,314,835 B1 | 11/2001 | Lascelles et al. |
| 6,387,066 B1 | 5/2002 | Whiteside |
| 6,440,093 B1 | 8/2002 | McEwen et al. |
| 6,472,795 B2 | 10/2002 | Hirose et al. |
| 6,494,798 B1 | 12/2002 | Onogi |
| 6,500,138 B1 | 12/2002 | Irby et al. |
| 6,517,503 B1 | 2/2003 | Naft et al. |
| 6,525,446 B1 | 2/2003 | Yasuda et al. |
| 6,527,671 B2 | 3/2003 | Paalasmaa et al. |
| 6,533,742 B1 | 3/2003 | Gach, Jr. |
| 6,537,175 B1 | 3/2003 | Blood |
| 6,554,773 B1 | 4/2003 | Nissila et al. |
| 6,572,558 B2 | 6/2003 | Masakov et al. |
| 6,599,255 B2 | 7/2003 | Zhang |
| 6,659,910 B2 | 12/2003 | Gu et al. |
| 6,666,796 B1 | 12/2003 | MacCready, Jr. |
| 6,689,075 B2 | 2/2004 | West |
| 6,694,833 B2 | 2/2004 | Hoehn et al. |
| 6,709,411 B1 | 3/2004 | Olinger |
| 6,796,926 B2 | 9/2004 | Reinkensmeyer et al. |
| 6,805,677 B2 | 10/2004 | Simmons |
| 6,821,262 B1 | 11/2004 | Muse et al. |
| 6,827,579 B2 | 12/2004 | Burdea et al. |
| 6,836,744 B1 | 12/2004 | Asphahani et al. |
| 6,872,187 B1 | 3/2005 | Stark et al. |
| 6,878,122 B2 | 4/2005 | Cordo |
| 6,936,994 B1 | 8/2005 | Gimlan |
| 6,966,882 B2 | 11/2005 | Horst |
| 7,041,069 B2 | 5/2006 | West |
| 7,124,321 B2 | 10/2006 | Garnett et al. |
| 7,137,938 B2 | 11/2006 | Gottlieb |
| 7,171,331 B2 | 1/2007 | Vock et al. |
| 7,190,141 B1 | 3/2007 | Ashrafiuon et al. |
| 7,192,401 B2 | 3/2007 | Saalasti et al. |
| 7,239,065 B2 | 7/2007 | Horst |
| 7,252,644 B2 | 8/2007 | Dewald et al. |
| 7,309,320 B2 | 12/2007 | Schmehl |
| 7,324,841 B2 | 1/2008 | Reho et al. |
| 7,365,463 B2 | 4/2008 | Horst et al. |
| 7,410,471 B1 | 8/2008 | Campbell et al. |
| 7,416,537 B1 | 8/2008 | Stark et al. |
| 7,431,707 B2 | 10/2008 | Ikeuchi |
| 7,457,724 B2 * | 11/2008 | Vock et al. .............. 702/182 |
| 7,458,922 B2 | 12/2008 | Pisciottano |
| 7,537,573 B2 | 5/2009 | Horst |
| 7,559,909 B2 | 7/2009 | Katoh et al. |
| 7,578,799 B2 | 8/2009 | Thorsteinsson et al. |
| 7,648,436 B2 | 1/2010 | Horst et al. |
| 7,731,670 B2 | 6/2010 | Aguirre-Ollinger et al. |
| 7,833,178 B2 | 11/2010 | Lee et al. |
| 7,880,345 B2 | 2/2011 | Hoffmann et al. |
| 7,998,092 B2 | 8/2011 | Avni et al. |
| 8,167,829 B2 | 5/2012 | Sterling et al. |
| 2001/0029343 A1 | 10/2001 | Seto et al. |
| 2002/0128552 A1 | 9/2002 | Nowlin et al. |
| 2003/0104886 A1 | 6/2003 | Gajewski |
| 2003/0120183 A1 | 6/2003 | Simmons |

(56) References Cited

U.S. PATENT DOCUMENTS

| | | |
|---|---|---|
| 2003/0195638 A1 | 10/2003 | Kajitani et al. |
| 2003/0212356 A1 | 11/2003 | Scorvo |
| 2004/0015112 A1 | 1/2004 | Salutterback et al. |
| 2004/0049139 A1 | 3/2004 | Craciunescu |
| 2004/0054311 A1 | 3/2004 | Sterling |
| 2004/0078091 A1 | 4/2004 | Elkins |
| 2004/0106881 A1 | 6/2004 | McBean et al. |
| 2005/0014600 A1 | 1/2005 | Clauson |
| 2005/0085346 A1 | 4/2005 | Johnson |
| 2005/0085353 A1 | 4/2005 | Johnson |
| 2005/0101887 A1 | 5/2005 | Stark et al. |
| 2005/0151420 A1 | 7/2005 | Crombez et al. |
| 2005/0173994 A1 | 8/2005 | Pfister et al. |
| 2005/0210557 A1 | 9/2005 | Falconer |
| 2005/0221926 A1 | 10/2005 | Naude |
| 2005/0245849 A1 | 11/2005 | Cordo |
| 2005/0251067 A1 | 11/2005 | Terry |
| 2005/0273022 A1 | 12/2005 | Diaz et al. |
| 2006/0004265 A1 | 1/2006 | Pulkkinen et al. |
| 2006/0069336 A1 | 3/2006 | Krebs et al. |
| 2006/0132069 A1 | 6/2006 | Hemphill et al. |
| 2006/0157010 A1 | 7/2006 | Moriwaki et al. |
| 2006/0206045 A1 | 9/2006 | Townsend et al. |
| 2006/0249315 A1 | 11/2006 | Herr et al. |
| 2006/0251179 A1 | 11/2006 | Ghoshal |
| 2006/0293624 A1 | 12/2006 | Enzerink et al. |
| 2007/0015611 A1 | 1/2007 | Noble et al. |
| 2007/0055163 A1 | 3/2007 | Asada et al. |
| 2007/0155557 A1 | 7/2007 | Horst et al. |
| 2007/0155558 A1 | 7/2007 | Horst et al. |
| 2007/0155560 A1 | 7/2007 | Horst et al. |
| 2007/0155588 A1 | 7/2007 | Stark et al. |
| 2007/0162152 A1 | 7/2007 | Herr et al. |
| 2007/0173747 A1 | 7/2007 | Knotts |
| 2007/0225620 A1 | 9/2007 | Carignan et al. |
| 2007/0265534 A1 | 11/2007 | Martikka et al. |
| 2007/0270265 A1 | 11/2007 | Miller et al. |
| 2007/0287928 A1 | 12/2007 | Kiviniemi et al. |
| 2008/0039731 A1 | 2/2008 | McCombie et al. |
| 2008/0097269 A1 | 4/2008 | Weinberg et al. |
| 2008/0195005 A1 | 8/2008 | Horst et al. |
| 2008/0200994 A1 | 8/2008 | Colgate et al. |
| 2008/0234608 A1 | 9/2008 | Sankai |
| 2009/0007983 A1 | 1/2009 | Healy |
| 2009/0036894 A1 | 2/2009 | Horst |
| 2009/0048686 A1 | 2/2009 | Ikeuchi et al. |
| 2009/0131839 A1 | 5/2009 | Yasuhara |
| 2009/0171469 A1 | 7/2009 | Thorsteinsson et al. |
| 2009/0204038 A1 | 8/2009 | Smith et al. |
| 2009/0235739 A1* | 9/2009 | Morris Bamberg ........ 73/379.05 |
| 2009/0260426 A1 | 10/2009 | Lieberman et al. |
| 2009/0306548 A1 | 12/2009 | Bhugra et al. |
| 2010/0038983 A1 | 2/2010 | Bhugra et al. |
| 2010/0039052 A1 | 2/2010 | Horst et al. |
| 2010/0049102 A1 | 2/2010 | Yasuhara |
| 2010/0113986 A1 | 5/2010 | Ashihara et al. |
| 2010/0114329 A1 | 5/2010 | Casler et al. |
| 2010/0125229 A1 | 5/2010 | Rudolph et al. |
| 2010/0234775 A1 | 9/2010 | Yasuhara et al. |
| 2010/0256537 A1 | 10/2010 | Menga |
| 2010/0280628 A1 | 11/2010 | Sankai |
| 2010/0298746 A1 | 11/2010 | Shimizu et al. |
| 2010/0318006 A1 | 12/2010 | Horst |
| 2011/0175744 A1* | 7/2011 | Englert et al. ................ 340/665 |
| 2012/0095377 A1 | 4/2012 | Smith et al. |
| 2012/0316475 A1 | 12/2012 | Bhugra et al. |
| 2013/0079687 A1 | 3/2013 | Horst et al. |
| 2013/0165817 A1 | 6/2013 | Horst et al. |

FOREIGN PATENT DOCUMENTS

| | | | |
|---|---|---|---|
| JP | 63-136978 A | | 6/1988 |
| JP | 02-275162 A | | 11/1990 |
| JP | 04-104180 A | | 4/1992 |
| JP | 05-038948 A | | 2/1993 |
| JP | 05-260766 | | 10/1993 |
| JP | 06-038551 A | | 2/1994 |
| JP | 07-274540 A | | 10/1995 |
| JP | 08-033360 A | | 2/1996 |
| JP | 08-149858 | | 6/1996 |
| JP | 08-154304 A | | 6/1996 |
| JP | 09-133196 A | | 5/1997 |
| JP | 09-261975 A | | 10/1997 |
| JP | 2001-353675 A | | 12/2001 |
| JP | 2002-191654 A | | 7/2002 |
| WO | WO 90/11049 A1 | | 10/1990 |
| WO | WO 2005/057054 A1 | | 6/2005 |
| WO | WO 2007/027673 A2 | | 3/2007 |
| WO | WO 2007/041303 A2 | | 4/2007 |

OTHER PUBLICATIONS

Advanced Mechatronics Lab (Univ. of Tokyo); Dual Excitation Multiphase Electrostatic Drive (DEMED); http://www.intellect.pe.u-tokyo.ac.jp/research/es_motor/demed_e.html; pp. 1-5; (printed) Nov. 21, 2002.

Advanced Mechatronics Lab (Univ. of Tokyo); High-power electrostatic motor; http://www.intellect.pe.u-tokyo.ac.jp/research/es_motor/es_motor_e.html; pp. 1-2; (printed) Nov. 21, 2002.

Advanced Mechatronics Lab (Univ. of Tokyo); Pulse driven induction electrostatic motor; http://www.intellect.pe.u-tokyo.ac.jp/research/es_motor/pim_e.html; pp. 1-5; (printed) Nov. 21, 2002.

Asel (Univ. of Delaware); Powered orthosis project; http://www.asel.udel.edu/robotics/orthosis/orthosis.html, 1 pg.; (update) Jan. 17, 1999.

British Tech. Group; Demonstration of energy saving in vehicles by integrating an infinitely variable transmission with an optimized petrol engine; prj. No. TR/00087/92; pp. 1-19; (version) Jul. 15, 1998.

Coronel et al; The Coronet effect positively infinitely variable transmission; U.C. Davis; No. 04CVT-51; pp. 1-8; 2004.

Fitch, C. J.; Development of the electrostatic clutch; IBM Journal; pp. 49-56; Jan. 1957.

Frank, Andrew; Engine optimization concepts for CVT-hybrid system to obtain the best performance and fuel efficiency; U.C. Davis; No. 04CVT-56; pp. 1-12; 2004.

Gongola et al.; Design of a PZT-actuated proportional drum brake; IEEE ASME Trans. on Mech.; vol. 4; No. 4; pp. 409-416; Dec. 1999.

Howard Leitch, PPT LTD.; Waveform Gearing; Motion System Design; pp. 33-35; Nov. 2002.

James et al.; Increasing power density in a full toroidal variator; 3rd Int'l. IIR-Symposium; Innovative Automotive Transmission; pp. 1-11; Dec. 2004.

Kawamoto et al.; Power assist system HAL-3 for GAIT disorder person; ICCHP 2002; LNCS 2398; pp. 196-203; 2002.

Kim et al.; On the energy efficiency of CVT-based mobile robots; Proc. 2000 IEEE; Int. Conf. on Robotics & Automation; pp. 1539-1544; San Francisco, CA; Apr. 2000.

Kluger et al.; An overview of current automatic, manual and continuously variable transmission efficiencies and their projected future improvements; Int. Congress and Expo. (No. 1999-1-1259); pp. 1-6; Detroit, MI; Mar. 1-4, 1999.

Krebs et al.; A paradigm shift for rehabilitation robotics; Eng. In Medicine and Biology Magazine, IEEE; vol. 27; Issue 4; pp. 61-70; Jul. 2008.

Misuraca et al.; Lower limb human enhancer; Int. Mech. Eng. Conf. and Expo.; New York, NY; pp. 1-7; Nov. 11-16, 2001.

Niino et al.; Electrostatic artificial muscle: compact, high-power linear actuators with multiple-layer structures; Proc. IEEE Workshop on Micro Electro Mechanical Systems; Oiso, Japan; pp. 130-135; Jan. 1994.

Nugent, James; Design and performance of an exponential roller gear continuously variable transmission with band clutches; U.C. Davis; No. 04CVT-18; pp. 1-8; 2004.

Ohhashi, Toshio et al.; Human perspiration measurement; Physiological Measurement; vol. 19; pp. 449-461; 1998.

(56) References Cited

OTHER PUBLICATIONS

Otto Bock Health Care; (3C100 C-Leg® System) Creating a new standard for prosthetic control; http://www.ottobockus.com/products/op_lower_cleg.asp; pp. 1-2; (printed) Nov. 22, 2002.

Otto Bock Health Care; (3C100 C-Leg® System) New generation leg system revolutionizes lower limb prostheses; http://www.ottobockus.com/products/op_lower_cleg4.asp; pp. 1-2; (printed) Nov. 22, 2002.

Otto Bock Health Care; Sensor Walk White Paper; ID No. 09031595.1; pp. 1-12; 2009.

Patras et al.; Electro-rheological fluids in the design of clutch systems for robotic applications; IEEE; pp. 554-558; Nov. 11-13, 1992.

Powell et al.; Computer model for a parallel hybrid electric vehicle (PHEV) with CVT; Proc. AACC; pp. 1011-1015; Chicago, IL; Jun. 2000.

Shastri et al.; Comparison of energy consumption and power losses of a conventionally controlled CVT with a servo-hydraulic controlled CVT and with a belt and chain as the torque transmitting element; U.C. Davis; No. 04CVT-55; pp. 1-11; 2004.

Shriner's Hospitals; Your new orthosis; http://www.shrinershq.org/patientedu/orthosis.html; pp. 1-3; (printed) Nov. 22, 2002.

Takaki et al; Load-sensitive continuously variable transmission for powerful and inexpensive robot hands; IEEE; pp. 45-46; 2004.

Takesue et al.; Development and experiments of actuator using MR fluid; IEEE; pp. 1838-1843; 2000.

Townsend Design; Functional Bracing Solutions (AIR Townsend & Ultra AIR); http://www.townsenddesign.com/air.html; 2 pgs; (printed) Nov. 21, 2002.

Townsend Design; Functional Knee Bracing Solutions; http://www.townsenddesign.com/functional.html; pp. 1; (printed) Nov. 21, 2002.

Townsend Design; Patented Motion Hinge (Planes of Motion); http://www.townsenddesign.com/motion.html; pp. 1; (printed) Nov. 21, 2002.

Trimmer et al.; An operational harmonic electrostatic motor; IEEE; pp. 13-16; 1989.

Smith et al., U.S. Appl No. 12/471,299 entitled "Therapy and mobility assistance system," filed May 22, 2009.

Bhugra, Kern; U.S. Appl. No. 12/363,567 entitled "System and method for controlling the joint motion of a user based on a measured physiological property," filed Jan. 30, 2009.

* cited by examiner

| Size | Foot[3] resistor HP | Foot[2] resistor BO | Foot[1] resistor HA | Foot[0] resistor BI | Description |
|---|---|---|---|---|---|
| 0 (small) | 8K | 8K | 8K | 8K | Smallest size |
| 1 (med) | 8K | 8K | 8K | 10K | |
| 2 | 8K | 8K | 10K | 8K | |
| 3 | 8K | 8K | 10K | 10K | Largest ball with shortest heel |
| 4 | 8K | 10K | 8K | 8K | Smallest ball with largest heel |
| 5 | 8K | 10K | 8K | 10K | |
| 6 (large) | 8K | 10K | 10K | 8K | |
| 7 (XL) | 8K | 10K | 10K | 10K | Largest size |
| 8-15 | 10K | x | x | x | Add rows as needed for nonstandard sizes |

FIGURE 9

FOOT PAD DEVICE AND METHOD OF OBTAINING WEIGHT DATA

CROSS-REFERENCE TO RELATED APPLICATIONS

This application claims the benefit of U.S. Provisional Application No. 61/151,103, filed 9 Feb. 2009, which is incorporated in its entirety by this reference.

TECHNICAL FIELD

This invention relates generally to the foot device field, and more specifically to an improved foot sensor system in the foot sensor device field.

BACKGROUND

Foot sensors are useful in several applications that require weight data and other information related to how and when a person places their foot on the ground. For example, assistive devices such as active orthoses and active prosthetics require sensor input from beneath the foot of the person to determine gait and to optimize assistance. As another example, patient monitoring devices such as those to assess balance and analyze gait require foot sensors to gather data.

Current devices that use foot sensors to obtain weight data have several drawbacks. To obtain accurate readings, many devices include multiple sensors (on the order of a dozen or more), which increase the cost and complexity of the device. Current devices are also unable to automatically detect and/or automatically compensate for a broken sensor, which is crucial to device functionality and operability. Furthermore, any malfunction in transmission of foot sensor information (including force data and foot pad sizing details) due to faults, such as a broken cable or connector, will also reduce or inhibit proper device operation if the device is unable to automatically verify sensor connectivity or verify the correct size of the foot sensor. Finally, current device performance often varies with other factors outside of the control or understanding of the device, such as tightness of the person's shoe, which can adversely affect device functionality since current devices do not calibrate and compensate for such additional variable factors.

Thus, there is a need in the foot sensor field to create an improved foot sensor. This invention provides such an improved foot pad device and method of obtaining weight data.

BRIEF DESCRIPTION OF THE FIGURES

FIG. 9 is a partial table of resistor values for various sensor locations and foot pad sizes for one version of the foot pad device.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method of Obtaining Weight Data with Automatic Calibration

Figure 1:
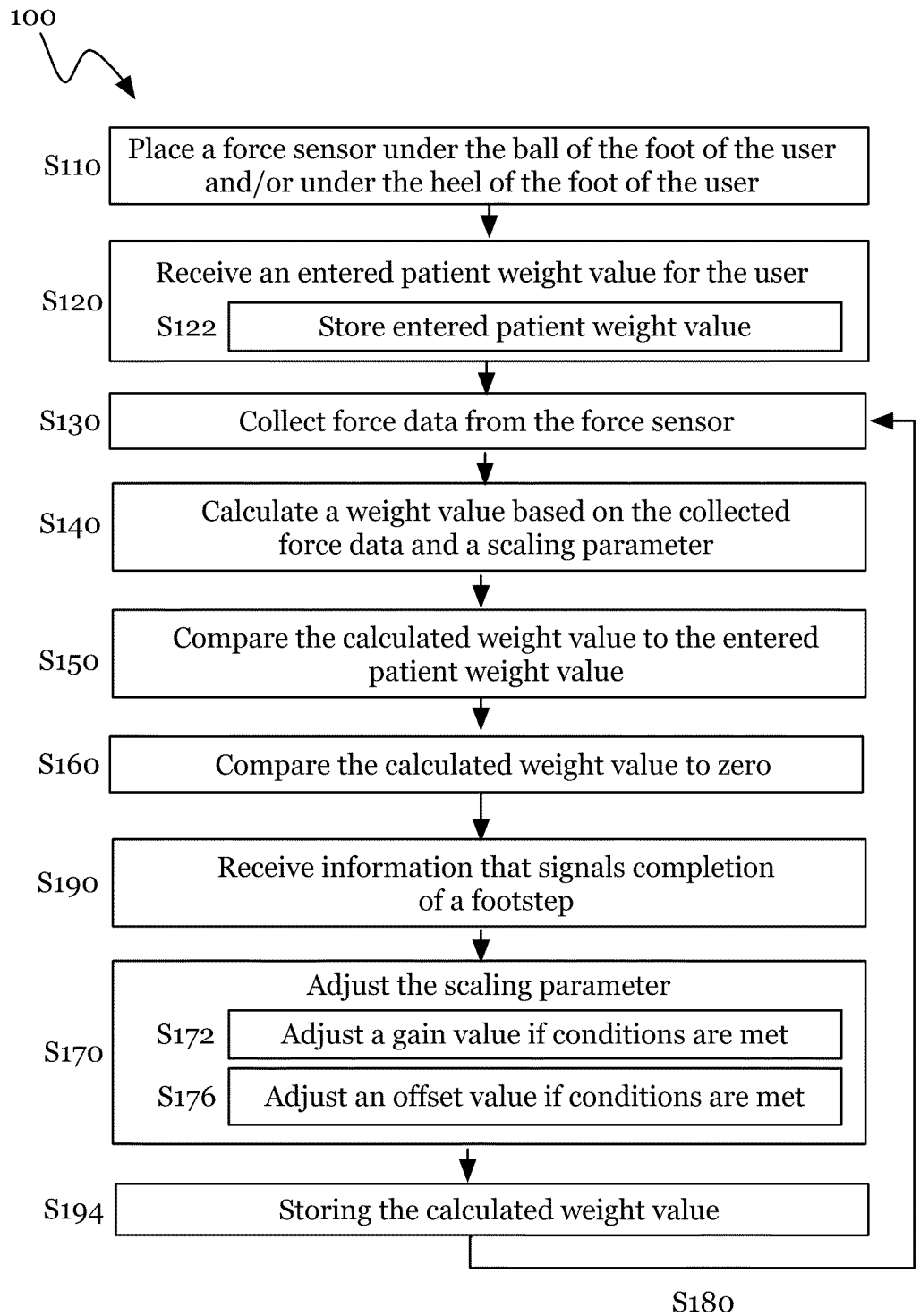
FIG. 1 is a schematic of the first preferred embodiment of the method.

In a first preferred embodiment, the method of obtaining weight data 100 with automatic calibration is preferably used to obtain weight data from a force sensor in a foot pad worn by a user. As shown in FIG. 1, the method preferably includes the steps of placing the force sensor under the ball of the foot of the user and/or under the heel of the foot of the user S110; receiving an entered patient weight value for the user S120; collecting force data from the force sensor S130; calculating a weight value based on the collected force data and a scaling parameter that scales the collected force data S140; comparing the calculated weight value to the entered patient weight value in a first comparison S150; comparing the calculated weight value to zero in a second comparison S160; adjusting the scaling parameter based on at least one of the first and second comparisons S170; and step S180 of periodically repeating one or more of the above steps. The steps of collecting force data S130, calculating a weight value S140, comparing the calculated weight value to the entered patient weight value S150, comparing the calculated weight value to zero S160, and adjusting the scaling parameter S170 are preferably repeated periodically for each of a plurality of force sensors in the foot pad, but may alternatively be repeated periodically for a single force sensor in the foot pad, or repeated periodically for only a portion of a plurality of force sensors in the foot pad. Some embodiments of the method 100 may further include the steps of storing the calculated weight value.

The method of obtaining weight data with automatic calibration is preferably performed to gather weight data that is applied to selectively control an active mobility assistance device that enhances the mobility of the leg of the user (such as an active orthotic device or an active prosthetic device), to a patient monitoring device, or to any suitable device that collects and/or analyzes weight-on-foot data. As an example, the method may be performed to gather data that an active assistance device uses to determine how to control an actuator that applies assistance and/or resistance to movement. The method preferably automatically calibrates to compensate for spurious and/or affected weight readings. For example, the method may provide an active assistance device with weight data that cancels the effects of apparent weight readings that are due to external circumstances, such as foot-stomping, an uneven or compliant floor surface, tight shoelaces or other fasteners, or drift in sensor reading and other electronics caused by environment changes like ambient temperature and humidity. As another example, the method may continue to obtain weight readings that take into account when a sensor shifts position relative to the foot of the user, or when only a portion of the total weight of the user is applied to the sensor. As another example, the method preferably obtains weight readings that compensate for weight that is offloaded to a cane or walker, allowing an active orthotic or prosthetic device to continue correct operation.

Step S110, which includes placing the force sensor under the ball of the foot of the user and/or under the heel of the foot of the user, functions to strategically position the force sensor relative to the foot of the user. The step preferably includes placing one force sensor in an inside (i.e., medial) ball position, placing one force sensor in an outside (i.e., lateral) ball position, placing one force sensor in an anterior heel position, and/or placing one force sensor in a posterior heel position. The step of placing the force sensor may alternatively and/or additionally include placing a force sensor under the arch of the foot, placing a force sensor under the toes of the foot, and/or placing a force sensor in any suitable location relative to the foot of the user. The force sensor is preferably a force sensitive resistor that changes electrical resistance value with changes in the force applied to the force sensor, but the foot sensor may alternatively be a pressure sensor combined with an air bladder, a piezoelectric sensor, a capacitive sensor, or any suitable type of sensor.

Step S120, which includes receiving an entered weight value, functions to obtain a known or initially estimated weight of the user. The step preferably includes receiving an entered weight value and storing the entered weight value to memory S122. The entered weight value may be entered by the user and/or any suitable operator, such as a physician or a researcher. The entered weight value is preferably stored by a processor to a memory chip, but may alternatively be stored by any suitable operator to any suitable storage medium, preferably such that the stored weight value is accessible.

Step S130, which includes collecting force data from the force sensor in the foot pad, functions to gather information from the force sensor. The step is preferably performed for each force sensor in the foot pad during the periodical repeating of the steps of the method. However, the step of collecting force data S130 may alternatively be performed for each of only a portion of force sensors in the foot pad. For example, multiple force sensors in a foot pad may be designated as either active or inactive, and the step of collecting force data is performed for each of the active force sensors. The step of collecting force data from the force sensor S130 is preferably performed by a processor, but may alternatively be collected manually by a person, or through any suitable method. The collected force data is preferably in the form of voltage, but may alternatively be in the form of current, resistance, capacitance, inductance, or any other suitable form.

Step S140, which includes calculating a weight value based on the collected force data and a scaling parameter that scales the collected force data, functions to convert the collected force data (i.e., raw data) into a meaningful weight value (i.e., processed data). The scaling parameter preferably includes a gain value and/or offset value. The gain value is preferably a multiplier value and the offset value is preferably an additive value, such that collected force data is multiplied by the gain value and/or summed with the offset value to become converted into a calculated weight value. In other words, the calculated weight is preferably expressed as a function of the collected force data, the gain value, and the offset value, such as (calculated weight)=(gain)*(collected raw force data)+(offset). The scaling parameter may be positive or negative, an integer or a fractional number, and/or have any suitable characteristic. A weight value is preferably calculated using collected force data from each force sensor in the foot pad. As an example, a weight value may be calculated for each collected force data value such that the number of calculated weight values is equal to the number of collected force data values. As another example, a weight value may be calculated from the average of collected force data values from two or more force sensors that cover overlapping areas in the foot pad, such that the number of calculated weight values is less than the number of collected force data values, but all collected force data values are utilized. However, the weight value may alternatively be calculated using collected force data from only a portion of force sensors in the foot pad. As an example, collected force data from each of two or more force sensors that cover overlapping areas in the foot pad may be functionally combined by calculating a weight value based on the maximum force data of the group of force sensors. The scaling parameter may be different for calculating weight values from different force sensors, or may be the same for calculating weight values from a portion or all force sensors. The step of calculating a weight value is preferably performed by a processor, which also determines the gain value and offset value.

The step of comparing the calculated weight value to the entered patient weight in a first comparison S150 and the step of comparing the calculated weight value to zero in a second comparison S160 function to provide information used to determine how to adjust the scaling parameter. As steps of the method repeat periodically during step S180, the results of the first and second comparisons are preferably used in the step of adjusting the scaling parameter S170 such as to periodically calibrate the calculated weight value calculated from the collected force data. In the preferred embodiment, the method further includes the step of receiving information that signals the completion of a footstep by the user S190. The signal of a completion of a footstep is preferably used, in addition to the first and second comparisons, in the step of adjusting the scaling parameter. The step of receiving information that signals the completion of a footstep by the user S190 preferably includes determining the completion of at least two interval portions that complete a footstep or gait cycle. Determining the completion of two interval portions is preferably involves analyzing force data from the force sensors. For example, a first interval portion may be the portion of a gait cycle between heel strike to toe off, the interval during which at least some of the user weight is on the foot and therefore on at least one of the force sensors (e.g., a nonzero calculated weight value, or a calculated weight value greater than a threshold above zero). At some point during this first interval portion, the full patient weight is expected to be on the foot pad. A second interval portion may be the portion of a gait cycle between toe off and heel strike of the subsequent footstep, the interval during which no weight is on the foot (e.g., a calculated weight value of zero or approximately zero within a threshold). The first and second intervals preferably combine to form an entire gait cycle. However, the first and second intervals may each be any suitable portion of a footstep that begins and ends at any suitable point in a gait cycle (for example, an entire footstep may range from toe-off to toe-off, or from heel strike to heel strike). In alternative embodiments, receiving information that signals completion of a footstep may include determining the completion of three or more intervals, each any suitable portion of a gait cycle. However, the step of receiving information that signals the completion of a footstep by the user may alternatively and/or additionally include analyzing sensor data from a knee angle sensor, analyzing accelerometer data, analyzing gyroscope data, analyzing the time lag between data from different force sensors in the foot pad, analyzing data from sensors on the surface on which the user takes the footstep, analyzing data from visual markers placed on the user, registering an interruption in an optical path (such as that between a light sensor and a laser or a light-emitting diode), receiving manual input by a person, and/or any suitable method of determining completion of a footstep by the user. The method may additionally and/or alternatively include receiving information that signals the beginning of a footstep by the user, which may involve detection methods similar those used in the step of receiving information that signals the completion of a footstep by the user.

Figure 2:
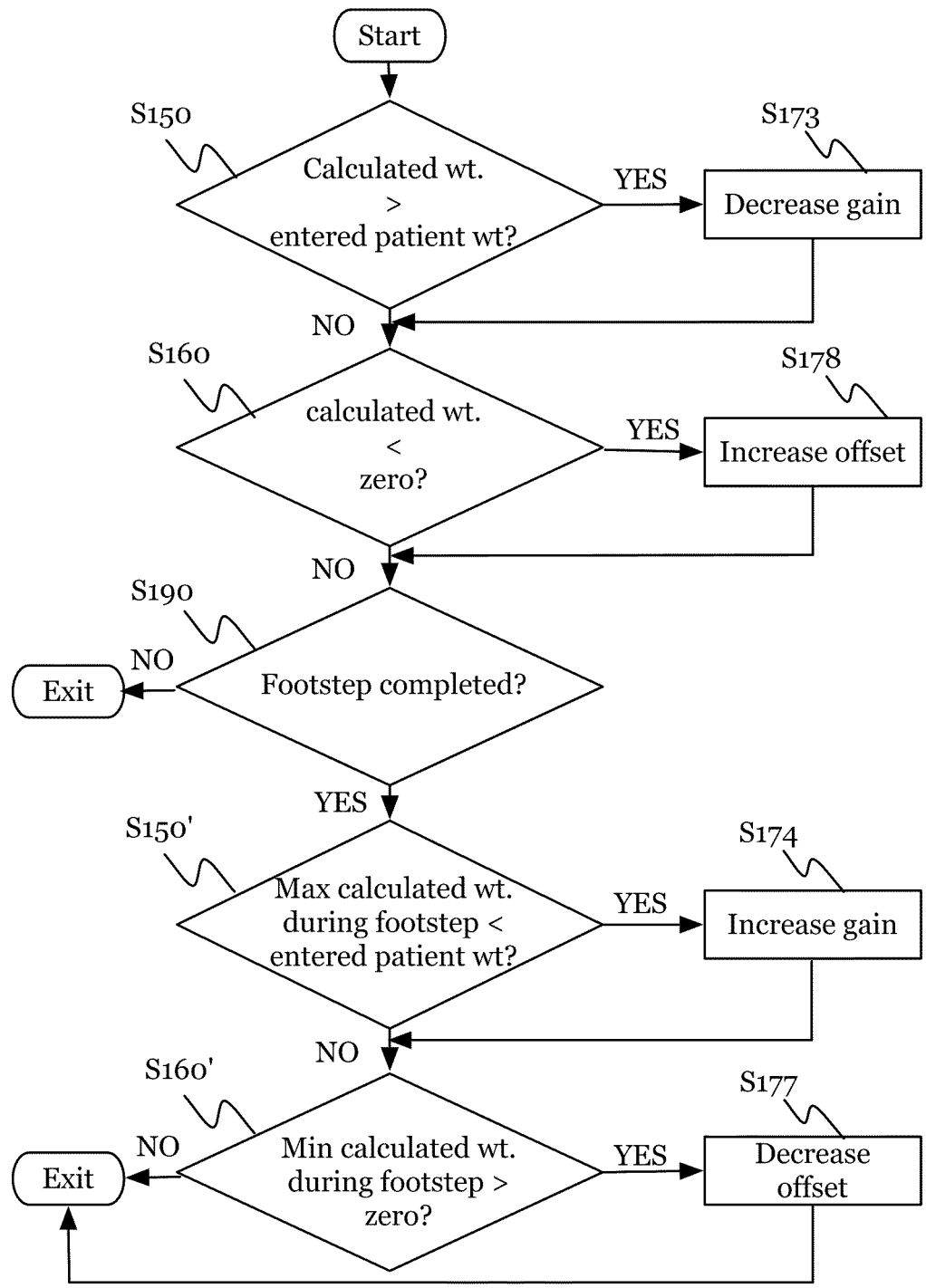
FIG. 2 is a detailed schematic of the step of adjusting the scaling parameter of the first preferred embodiment of the method.

As shown in FIG. 2, the step of comparing the calculated weight value to the entered patient weight in a first comparison S150 preferably has two variations. In a first variation, the step of comparing the calculated weight value to the entered patient weight S150 is performed without any knowledge of completion of a footstep. In this variation, the calculated weight value may be compared to the entered patient weight, or to the entered patient weight multiplied by a constant such as 1.2. In a second variation, the step of comparing the calculated weight value to the entered patient weight S150' is performed after receiving information signaling completion of a footstep, and preferably includes comparing the maximum calculated weight value calculated during the footstep to the entered patient weight. Similarly, the step of comparing the calculated weight value to zero S160 in a second comparison preferably has two variations. In a first variation, the step of comparing the calculated weight value to zero S160 is performed without any knowledge of completion of a footstep. In a second variation, the step of comparing the calculated weight value to zero S160' is performed after receiving information signaling completion of a footstep, and preferably includes comparing the minimum calculated weight value calculated during the footstep to zero. Each of the variations of steps S150 and S160 preferably provides information used in the step of adjusting the scaling parameter S170.

The step of adjusting the scaling parameter S170 functions to calibrate the conversion of the collected force data into a calculated weight value. As shown in FIG. 1, the step of adjusting the scaling parameter preferably includes adjusting a gain value S172 and/or adjusting an offset value S176.

Figure 3:
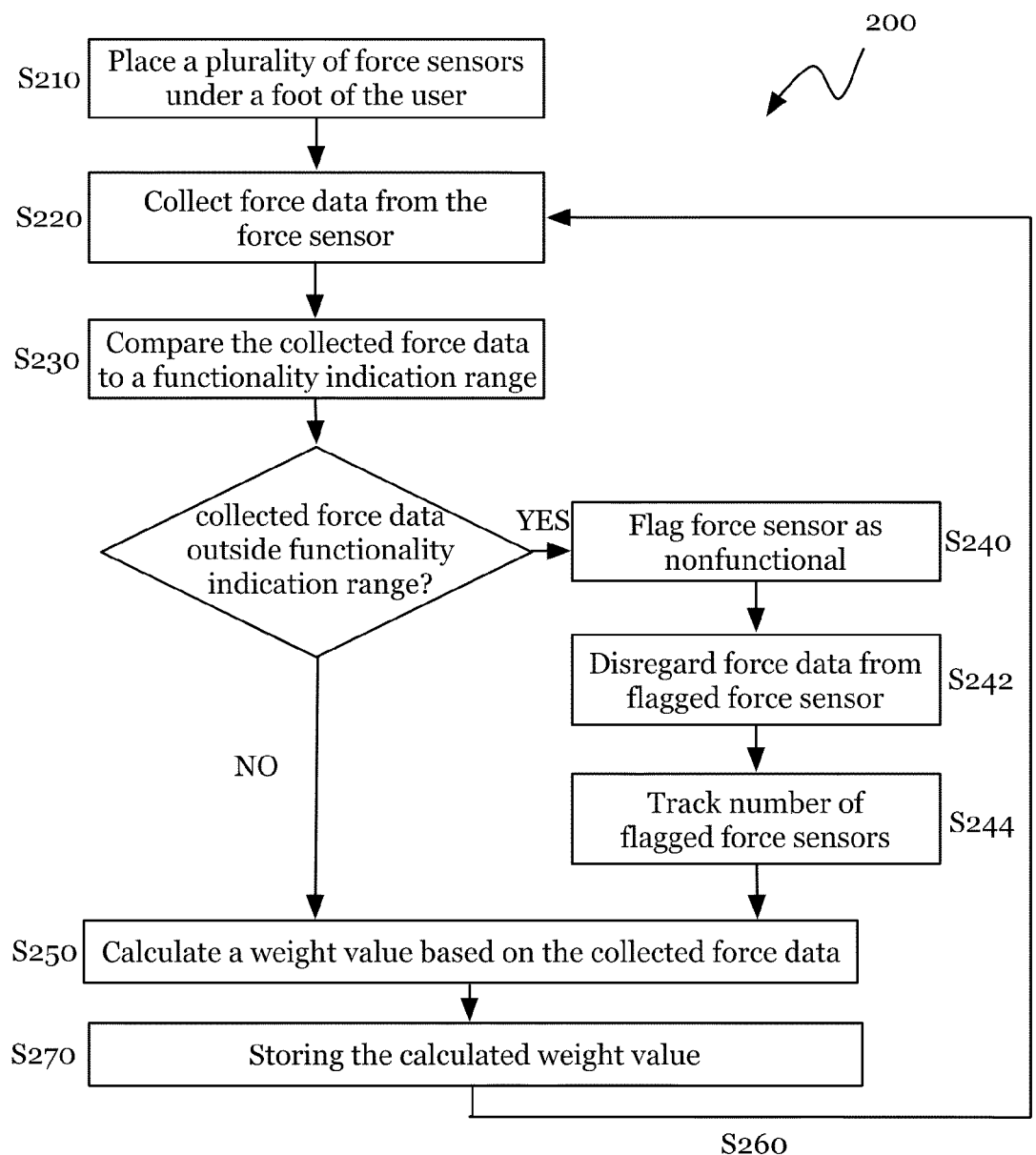
FIG. 3 is a schematic of the second preferred embodiment of the method.

As shown in FIGS. 2 and 3, the step of adjusting the gain value S172 preferably includes decreasing the gain value S173 if the calculated weight value is greater than the entered patient weight value; and/or increasing the gain value S174 if the user has completed a footstep and the maximum of the calculated weight values calculated during the footstep is less than the entered patient weight value. If a calculated weight at any time is greater than the entered patient weight value, decreasing the gain value S173 will decrease the next calculated weight value and calibrate the conversion of the collected force data to calculated weight value to result in a more accurate calculated weight value. In a preferred embodiment, the step of decreasing the gain value S173 is performed if the calculated weight value is greater than a threshold above the entered patient weight value. The threshold may, for example, be a percentage such as 20% above the entered patient weight value, or a set absolute amount of weight above the entered patient weight value applicable for a variety of entered patient weight values. The threshold preferably compensates for an expected increase in weight on foot due to ground impact force as the user completes footsteps, compared to a static entered patient weight. If the maximum weight value calculated throughout a footstep taken by the user (at some point during the step, the maximum expected weight, or the entered patient weight value, should be placed on the foot of the user) is less than the entered patient weight value, increasing the gain value S174 will increase the next calculated weight value and calibrate the conversion of the collected force data to calculated weight value to result in a more accurate calculated weight value. Decreasing the gain value S173 is preferably performed without any knowledge of the gait cycle phase of the user. Increasing the gain value S174 preferably may be performed only if the user is presumed to have completed a footstep, such as by receiving information that signals completion of a footstep by the user or receiving information that signals the beginning of a subsequent footstep. Increasing the gain is preferably not performed when the maximum possible user weight should not be placed on the foot of the user, such as when the user is sitting down, tapping their foot, or standing with weight on both feet. The amount by which the gain value is increased or decreased may be a constant number (such as +1 or −0.5), a number dependent on the scale of the calibration needed (such as based on the amount of difference in the first or second comparison), or any suitable number. The step of adjusting the gain value S172 is preferably performed automatically by the processor, but may alternatively and/or additionally be performed by a person such as the user, a physical therapist, or caregiver through a computer or other interface.

As shown in FIGS. 2 and 3, the step of adjusting the offset value S176 preferably includes decreasing the offset value S177 if the user has completed a footstep and the minimum of the calculated weight values calculated during the footstep is greater than zero; and/or increasing the offset value S178 if the calculated weight value is less than zero. If the minimum weight value calculated throughout a step taken by the user (at some point during the step, a minimum expected weight of zero should be placed on the foot of the user as the user lifts their foot off the ground) is greater than zero, decreasing the offset value S177 will decrease the next calculated weight value and calibrate the conversion of the collected force data to calculated weight value to result in a more accurate calculated weight value. If a calculated weight at any time is a (nonsensical) negative weight value less than zero, increasing the offset value S178 will increase the next calculated weight value and calibrate the conversion of the collected force data to calculated weight value to result in a more accurate calculated weight value. Decreasing the offset value S177 preferably may be performed only if the user is presumed to have completed a footstep, such as by receiving information that signals completion of a footstep by the user or receiving information that signals the beginning of a subsequent footstep. Increasing the offset value S178 preferably may be performed at any time without any knowledge of the gait cycle phase of the user. Similar to adjusting the gain value, the amount by which the offset value is increased or decreased may be a constant number (such as +1 or −0.5), a number dependent on the scale of the calibration needed, or any suitable number. The step of adjusting the offset value S176 is preferably performed automatically by the processor, but may alternatively and/or additionally be performed by a person such as the user, a physical therapist, or caregiver through a computer or other interface.

Step S180, which includes periodically repeating one or more of the above steps, preferably includes preparing for the subsequent cycle of steps of the method. Preparing for the subsequent cycle of steps of the method may include resetting the minimum weight calculated throughout a footstep taken by the user and the maximum weight value calculated throughout a footstep taken by the user. In resetting the minimum and maximum calculated weight values, the minimum and maximum calculated weight values may be erased from memory, set to zero, or set to any suitable values that effectively ensures that new minimum and maximum calculated weight values will be obtained in the next cycle. For example, resetting may include setting the minimum calculated weight to a high number and setting the maximum calculated weight to a low number, in which case the next cycle is expected to overwrite each of the minimum and maximum calculated weight values with new, potentially more accurate, values.

Figure 4:
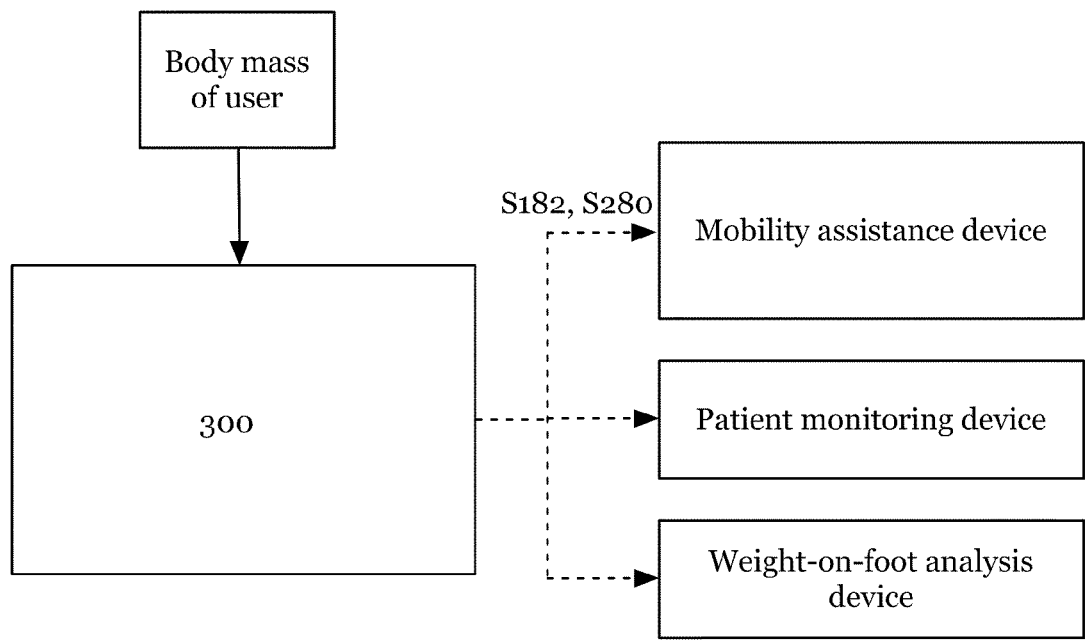
FIG. 4 is a schematic of information flow between a user, the foot pad device of the preferred embodiment, and applications of weight data.

In a preferred variation of the method as shown in FIG. 4, the method further includes applying the stored calculated weight to selectively control an actuator of a mobility assistance device to enhance the mobility of a leg of the user S182. The mobility assistance device is preferably an active orthotic device such as that described in U.S. Pat. No. 7,537,573 entitled "Active muscle assistance and resistance device and method", which is incorporated in its entirety by reference. However, the mobility assistance device may alternatively be an active prosthetic device, or any suitable mobility assistance device.

As shown in FIG. 1, in some variations of the method, the method may further include the step of storing the calculated weight value S194, which functions to retain the calculated weight value for future use. As an example, the stored calculated weight values may be compiled to create a log of calculated weight values, which may be used in real-time and/or intended for later use in a variety of applications such as: obtaining a continuous stream of weight-on-foot data for gait analysis, tracking consistency of raw force data provided by a force sensor, and tracking progress in gait training. The step of storing the calculated weight value S194 is preferably performed for each calculated weight. As an example, storing every calculated weight may provide a high-resolution log that stores every sample. However, the step of storing the calculated weight value may alternatively be performed for only a portion of calculated weights. As an example, the step of storing may include a lossy compression of the calculated weight, which may provide a low-resolution log with a smaller file size. The step of storing the calculated weight value S194 is preferably performed by the processor, but may alternatively and/or additionally be performed by a person such as the user, a physical therapist, or caregiver. However, the step of storing the calculated weight may alternatively include sending the calculated weight value to an external printer, logger, computer, or another device such as an active orthotic device or an active prosthetic device. Sending the calculated weight value may be performed through a cable or a wireless communications interface such as Bluetooth.

Other variations of the method include every combination and permutation of steps. As an example, the step of adjusting the offset value S176 may be performed before or after the step of adjusting the gain value S172. As another example, the step of adjusting the gain may be omitted, or the step of adjusting the offset may be omitted.

2. Method of Obtaining Weight Data with Fault Tolerance

In a second preferred embodiment of the method of obtaining weight data, the method of obtaining weight data 200 with fault tolerance is preferably used to obtain weight data from a force sensor in a foot pad worn by a user. As shown in FIG. 3, the method preferably includes the steps of: placing a plurality of force sensors under a foot of the user S210; collecting force data from the force sensor S220; comparing the force data to a functionality indication range S230; if the collected force data is outside the functionality indication range, flagging the force sensor as nonfunctional S240 and disregarding force data from the flagged force sensor S242; calculating a weight value based on the collected force data S250; and the step S260 of periodically repeating the steps of collecting force data, comparing the collected force data, flagging the force sensor, disregarding force data from the flagged force sensor, and calculating a weight value. Steps S220, S230, S240, S242, and S250 are preferably repeated periodically for each of a plurality of force sensors in the foot pad, but may alternatively be repeated periodically for a single force sensor in the foot pad, or repeated periodically for only a portion of a plurality of force sensors in the foot pad.

Like the method of obtaining weight data with automatic calibration, the method of obtaining weight data 200 with fault tolerance is preferably performed to gather weight data that is applied to selectively control an active mobility assistance device that enhances the mobility of the leg of the user (such as an active orthotic device or an active prosthetic device), to a patient monitoring device, or to any suitable device that incorporates, collects, and/or analyzes weight-on-foot data. As an example, the method may be performed to gather data that an active assistance device uses to determine how to control an actuator that applies assistance and/or resistance to movement. The method is preferably fault tolerant, in that the method obtains accurate weight values despite any faulty sensors, up to a predetermined point. For example, the method recognizes any broken sensors and adjusts to continue obtaining accurate weight values if one or more sensors are broken.

Step S210, which includes placing a plurality of force sensors under a foot of the user, functions to strategically position the force sensor relative to the foot of the user. The step preferably includes the step of placing at least one of the plurality of force sensor under at least one of the ball of the foot and the heel of the foot, which is preferably similar to Step S110 as described above. However, the step of placing a plurality of force sensors under a foot of the user S210 may alternatively include placing a plurality of force sensors in any suitable location.

Step S220, which includes collecting force data from the force sensor in the foot pad, functions to gather information from the force sensor. The step of collecting force data S220 is preferably similar to Step S130 as described above. Force data is preferably collected from multiple force sensors in the foot pad, allowing for wider coverage and redundancy.

Step S230, which includes comparing the force data to a functionality indication range, functions to provide a test whose results are used to determine whether the force sensor and/or its signal communication path is functioning normally. The functionality indication range is preferably a voltage range set by a resistor that is electrically connected relative to each force sensor. Alternatively, the functionality indication range may alternatively be a current range, a resistance range, a capacitance range, or any suitable kind of measure. A particular force sensor is preferably considered functional if the value of its force data is within the functionality indication range, and is preferably considered nonfunctional if the value of its force data is outside of the functionality indication range. For example, in a first category of force sensor errors with the signal processing circuit shown in FIG. 8, a broken sensor, absent force sensor, broken wire, broken connector or another portion of the force sensor connection path preferably produces a high voltage force data that is above the functionality indication range. As another example, in a second category of force sensor errors with the signal processing circuit shown in FIG. 8, a sensor shorted to ground or any portion of the force sensor connection path shorted to ground preferably produces a low voltage force data that is below the functionality indication range. The functionality indication range is preferably the same for force data from every force sensor. Alternatively, the functionality indication range may be the same for force data from a portion of force sensors, or the functionality indication range may be different for force data from every force sensor. The step of comparing the force data to a functionality indication range S230 is preferably performed by a processor, but may alternatively be performed manually by a person, or through any suitable method.

The steps of flagging the force sensor as nonfunctional S240 and disregarding force data from the flagged force sensor S242 are preferably performed if the collected force data is outside the functionality indication range. The step of flagging the force sensor as nonfunctional S240 functions to distinguish nonfunctional force sensors from functional force sensors. The step of flagging the force sensor S240 may include identifying an event and tracking the number of flagged force sensors S244. For example, the identified event may be of the first category (collected force data is above the functionality indication range) or second category (collected force data is below the functionality indication range) of force sensor errors as described above, which may include a broken force sensor, an absent force sensor, or a broken wire, connector or other portion of the force sensor connection path, or any suitable notable event that causes the collected force data to be outside the functionality indication range. The step of tracking the number of flagged force sensors S244 functions to maintain a count of flagged force sensors that is useful for determining when the foot pad is no longer reliable to use with the method. The method preferably continues to be performed when one force sensor has been flagged, and preferably continues to be performed when up to a predetermined number of force sensors have been tracked as flagged force sensors. The method preferably ceases to be performed when the predetermined number of force sensors have been tracked as flagged force sensors. The value of the predetermined number preferably depends on the specific application, the number of force sensors that are available in the foot pad, and/or the desired degree of accuracy in the weight values obtained by the method. In some variations, if the collected force data is outside the functionality indication range, the method further includes providing notification that at least one force sensor is nonfunctional, which may include providing notification of the category of force sensor error (e.g., a first category in which the collected force data is above the functionality indication range or a second category in which the collected force data is below the functionality indication range, as described in the examples). Providing such notifications, such as to a user or operator, may be advantageous, such as to alert of a nonfunctional sensor and the possible need for repair.

The step of disregarding force data from the flagged force sensor S242 functions to prevent force data from flagged nonfunctional force sensors from being used to calculate a weight value, thereby increasing accuracy of weight values obtained with the foot pad. The step may be accomplished in many ways, including flagging the force data, erasing the force data, de-indexing the force data, or any other suitable way of disregarding force data from the flagged force sensor S242.

Step S250, which includes calculating a weight value based on the collected force data, functions to convert the collected force data into a meaningful weight value. Except as noted below, the step of calculating a weight value S250 is preferably similar to the step S140 as described above. The step of calculating a weight value based on the collected force data S250 preferably is not performed using any disregarded force data from a flagged force sensor.

In some variations of the method, the method may further include the step of storing the calculated weight value S270 and/or applying the calculated weight value to selectively control an actuator of a mobility assistance device to enhance the mobility of a leg of the user S280, which are preferably similar to those steps S122 and S182, respectively, as described above.

Other variations of the method include every combination and permutation of steps of both the first and second preferred embodiments. For example, the method may include the steps of calculating a weight value based on the collected force data and a scaling parameter S140 and adjusting the scaling parameter S170 of the first embodiment of the method 100, in combination with the steps of comparing the collected force data to a functionality indication range S230 and flagging the force sensor as nonfunctional S240 if the collected force data is outside the functionality indication range of the second embodiment of the method.

3. Foot Pad Device

Figure 5:
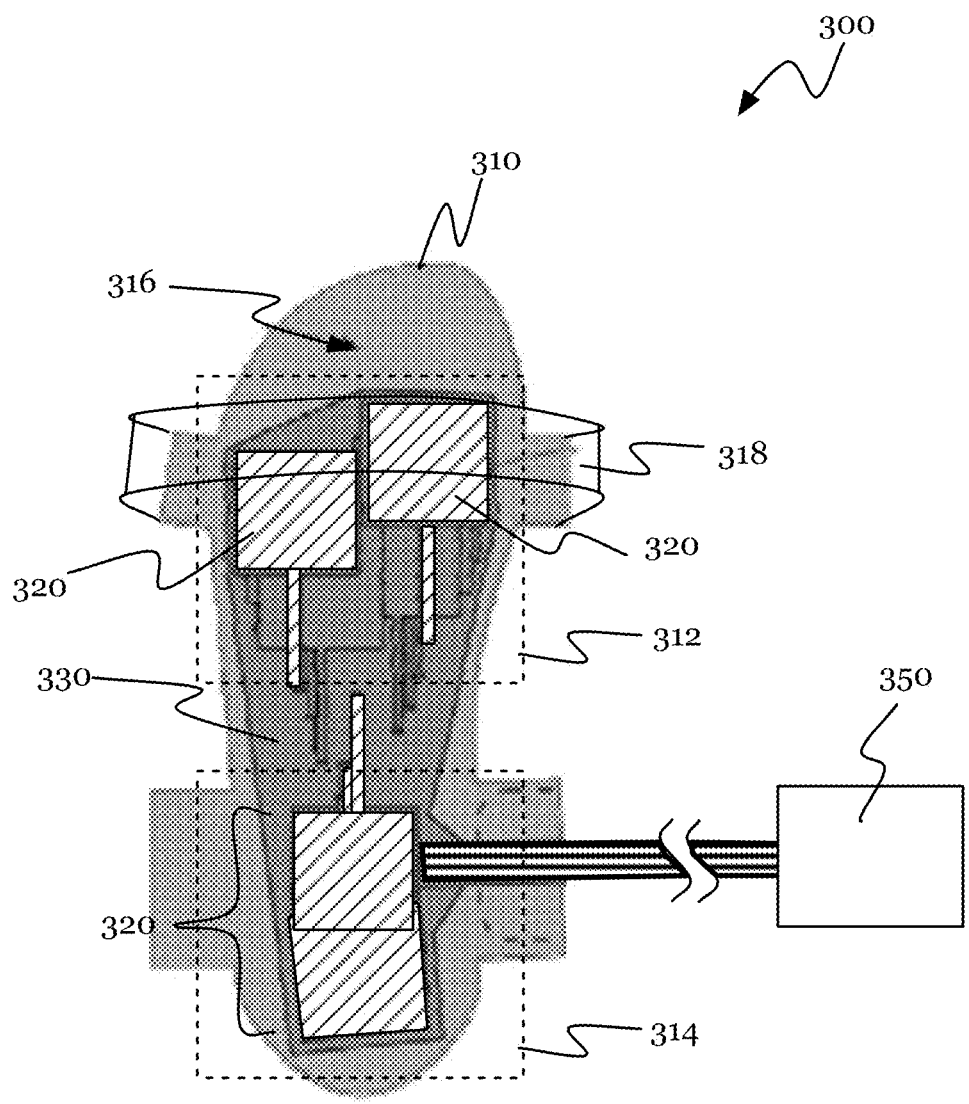
FIG. 5 is a transparent top view of one version of the foot pad device.

As shown in FIGS. 4 and 5, the foot pad device 300 of the preferred embodiments preferably includes a foot pad 310 worn on the foot of a user; a plurality of force sensors 320 that provide force data; sensor electronics 330 that condition the force data to be within a conditioned force data range; and a processor 350 that calculates a weight value based on the conditioned force data. The foot pad device 300 is preferably used to obtain weight values that are communicated to and applied to selectively control a mobility assistance device such as that described in U.S. Pat. No. 7,537,573, as referenced above. However, the foot pad device 300 may alternatively be used to obtain weight values that are communicated to another active assistance device (such as an active orthotic or active prosthetic), to a patient monitoring device, to any suitable device that incorporates weight-on-foot data, or to any suitable device that collects and/or analyzes weight-on-foot data. As an example, the foot pad device 300 may be integrated into a mobility assistance device, which may utilize the weight-on-foot data to determine how to control an actuator that applies assistance and/or resistance to movement. The foot pad device 300 is designed to compensate for spurious and/or affected weight readings and to be fault-tolerant.

The foot pad 310 of the foot pad device preferably functions to provide a wearable platform for the force sensors 320 of the foot pad device. The foot pad 310 preferably includes one or more regions in which force sensors 320 may be strategically placed to obtain force data from desired areas of the foot of the user. As shown in FIG. 5, the foot pad 310 preferably includes a ball region 312 that allows a force sensor to be positioned under the ball of the foot of the user, and/or a heel region 314 that allows a force sensor to be positioned under the heel of the foot of the user. However, the foot pad 310 may additionally and/or alternatively include an arch region, a toe region, a dorsal (top of foot) region, an ankle region, or any other suitable region in which to position a force sensor.

The foot pad 310 is preferably selected from a group of foot pads of different sizes, such as small, medium, large, and extra large. The group of foot pad sizes may alternatively and/or additionally include numbered sizes or more gradations of sizes. Alternatively, the foot pad 310 may be a universal single size. The foot pad 310 is preferably generally flat and extends under the sole of the foot of the user. The foot pad may additionally and/or alternatively wrap around the medial side, the lateral side, the dorsal side, and/or any suitable side of the foot, ankle, and/or lower leg. The foot pad may include padding and/or rigid structures to provide support to selected portions of the foot such as the arch. The foot pad may additionally and/or alternatively be integrated into a shoe and/or a device that includes a foot structure, such as an ankle-foot orthosis or a knee-ankle-foot orthosis.

As shown in FIG. 5, the foot pad 310 preferably includes surface textiles 316 (transparent in FIG. 5) that provide a comfortable interface for the foot of the user, and a strap 318 (transparent in FIG. 5) that helps secure and position the foot pad to the foot of the user. The foot pad 310 may alternatively have more than one strap, and/or omit the surface textiles and/or strap. The surface textiles 316 are preferably two pieces of adhesive-backed fabric that sandwich the force sensors and are cut into the approximate shape of a foot sole of the desired foot pad size. The surface textiles 316 may additionally and/or alternatively include an anti-microbial covering, adhesive covering, and/or a peel-off disposable covering, and may be coated or silk-screened with silicone or other suitable high friction material for traction. The strap 318 of the foot pad preferably is located near the ball region 312 and wraps over the toes of the user. The strap 318 may alternatively be located over the forefoot, midfoot, and/or hindfoot region of the foot pad, attached to wrap around the ankle, or any suitable portion of the foot pad. The strap 318 is preferably a strip of elastic webbing that stretches over the toes of the user and whose ends are sewn into the surface textiles. The strap 318 may alternatively be a strap that the user adjusts and/or fastens with fasteners such as a clasp, buckle, hook and loop fastener, hook and eye, or any other suitable fastener. The strap may additionally and/or alternatively be made of leather, string, the same material as the surface textiles 316, or any suitable material. The foot pad 310 may be side specific (e.g., designed for a left foot or for a right foot), or the foot pad 310 may be invertible to be used with either a left foot and a right foot, such as by flipping the foot pad so that the previous bottom face is the upper face, and inverting the strap 318 to wrap over the upper face.

The plurality of force sensors 320 of the foot pad device preferably functions to provide force data. The foot pad device preferably includes multiple force sensors to provide force data reflecting wider coverage of forces applied by the foot of the user, and to provide redundancy in that the foot pad device can continue to provide force data in the event of the failure of a portion of the force sensors. The foot pad preferably includes at least one force sensor located in the ball region 312 and/or heel region 314 of the foot pad 310. More preferably, as shown in FIG. 5, the foot pad includes two force sensors 320 in the ball region and two force sensors 320 in the heel region, such that one force sensor located at each of the following regions: an inside ball position (BI), an outside ball (BO) position, an anterior heel (HA) position, and a posterior heel (HP) position. However, a force sensor may alternatively be located at a portion of any the BI, BO, HA, and HP positions, at the arch region, the toe region, the dorsal region, the ankle region, and/or any suitable location on the foot pad. The exact locations of the force sensors 320 are preferably specific to the foot pad sizes, but the force sensors may alternatively be in the same locations for every size, or may be movable to adjust to different foot sizes and foot pad sizes. As shown in FIG. 6, for progressively larger foot pad sizes, the force sensors are preferably placed at an increased distance from the middle of the foot pad. This arrangement more accurately places the BI and BO force sensors (322 and 324, respectively) under the ball of the foot of the user, and the HA and HP force sensors (326 and 328, respectively) under the heel of the foot of the user. The force sensors are preferably embedded in the foot pad, but may alternatively be placed above, below, and/or on any exterior surface of the foot pad.

The force sensors 320 are preferably force sensitive resistors (FSRs) that change electrical resistance with changes in applied force, but each force sensor may alternatively be a pressure sensor combined with an air bladder, a piezoelectric sensor, a capacitive sensor, or any suitable type of sensor. The force sensors preferably provide force data in the form of voltage, but may alternatively be in the form of current, resistance, capacitance, and/or any other suitable form.

Figure 7:
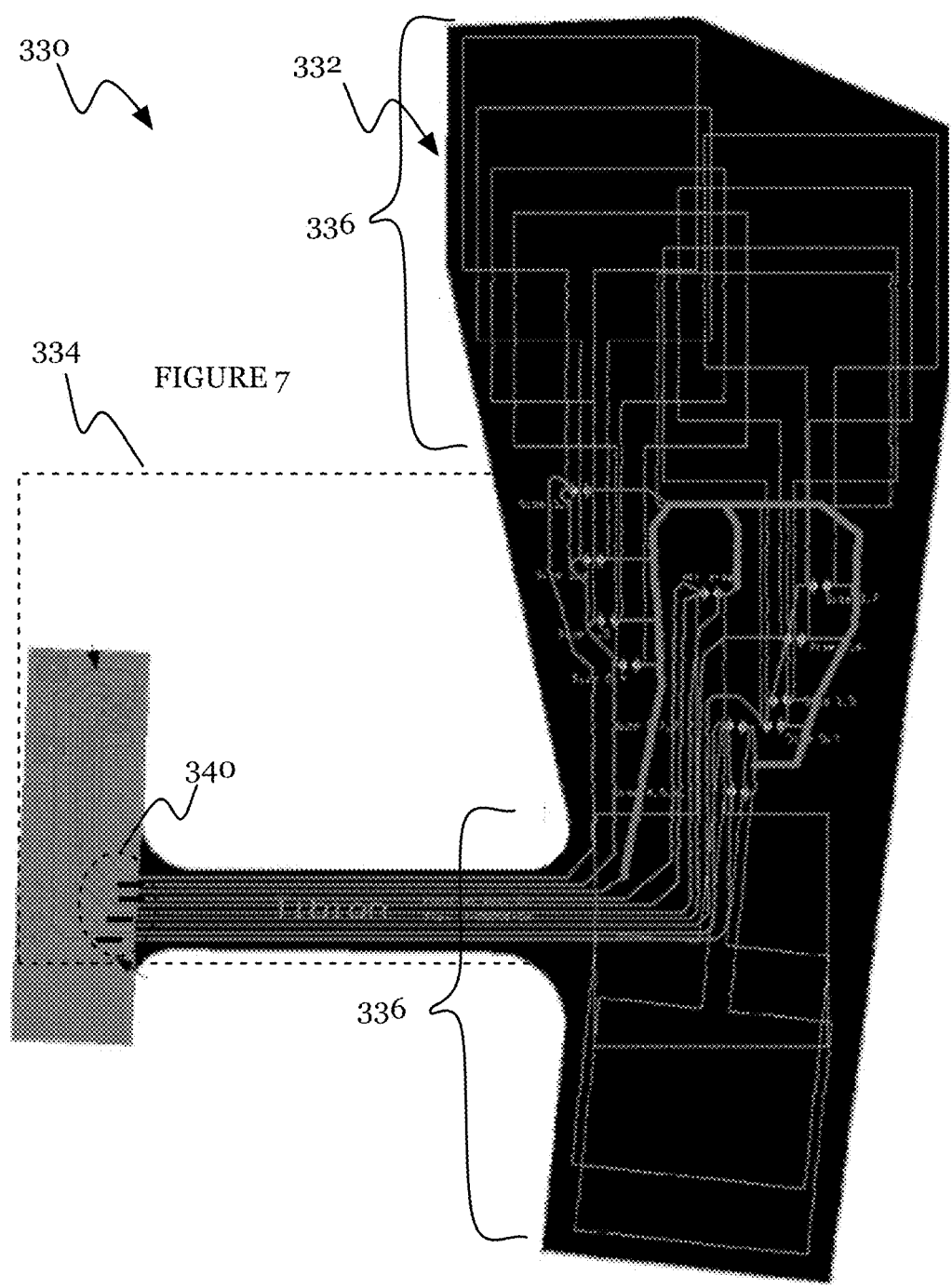
FIG. 7 is an illustration of one version of the sensor electronics of the foot pad device.

The sensor electronics 330 of the foot pad device 300 preferably function to condition the force data to be within a conditioned force data range. The conditioned force data range is preferably selected from a group of conditioned force data ranges. As shown in FIG. 7, the sensor electronics 330 preferably includes a flexible circuit 332 that preferably defines multiple applicable sensor positions 336 and includes multiple force sensor connections paths 334 adapted to transmit force data; and signal processing circuitry 338.

Figure 6A:
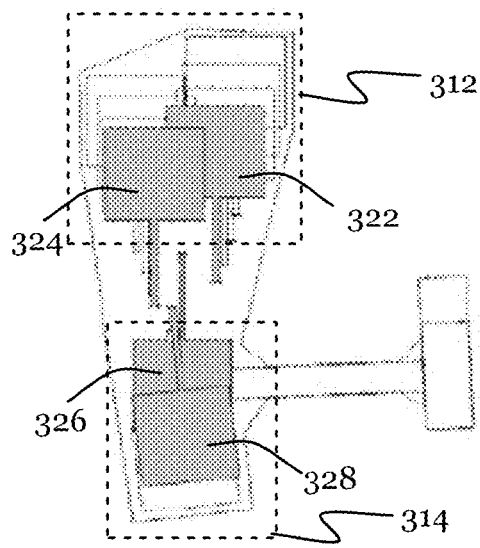
FIGS. 6A, 6B, 6C, and 6D are schematics of force sensor placement in one version of the foot pad device, for small, medium, large, and extra large foot pad sizes, respectively.
Figure 6B:
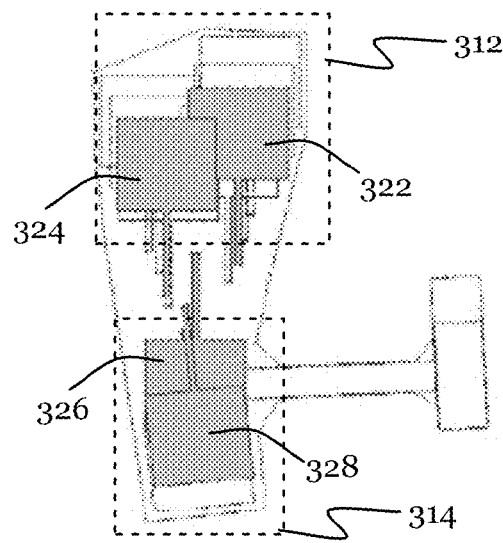
Figure 6C:
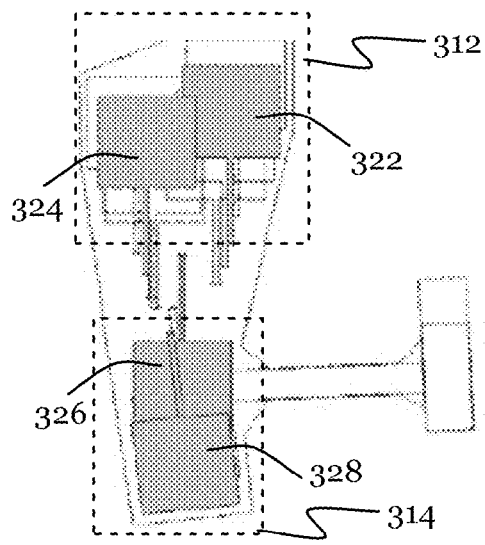
Figure 6D:
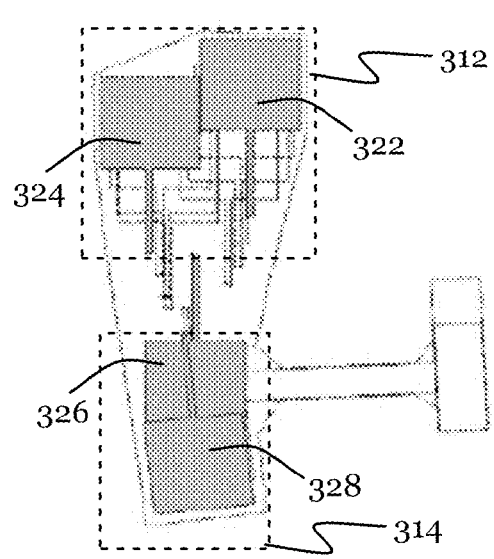

The flexible circuit 332 preferably functions to provide a flexible platform to which the force sensors connect. The circuit is preferably flexible to absorb energy from impact of the foot of the user, and to bend and conform to most motions of the foot. In other embodiments, the force sensors may attach to a rigid or semi-rigid circuit. A single flexible circuit design is preferably designed for use in all foot pad sizes, but the flexible circuit is preferably used in different ways for different foot pad sizes. Alternatively, multiple flexible circuit designs may be designed and used for different foot pad sizes. The set of sensor positions 336 of the flexible circuit 332 preferably are defined by pre-marked indications applicable for force sensor placement. As shown in FIG. 6, the applicable sensor positions 336 for force sensor placements are preferably outlines of force sensors (such as square outlines for square FSRs) drawn on the flexible circuit 332 in predesignated locations. The number of applicable sensor positions 336 preferably is greater than the number of force sensors, such that the force sensors are located in a selected portion of sensor positions 336. However, the number of applicable sensor positions 336 may alternatively be equal to the number of force sensors, or may be less than the number of force sensors such that at least a portion of the force sensors overlap and share a sensor position. The selected portion of sensor positions 336 where force sensors are located on the flexible circuit is preferably based on the foot pad size. As exemplified in FIG. 6A, a force sensor arrangement on the flexible circuit for a small foot pad size includes the BI and BO force sensors (322 and 324, respectively) located in the most posterior pre-marked sensor positions in the ball region, and the HA and HP force sensors (326 and 328, respectively) located in the most anterior pre-marked sensor positions in the heel region (all force sensors closest to the middle of the foot). As exemplified in FIG. 6D, a force sensor arrangement on the flexible circuit for an extra large foot pad size includes the BI and BO force sensors (322 and 324, respectively) located in the most anterior pre-marked sensor positions in the ball region, and the HA and HP force sensors (326 and 328, respectively) located in the most posterior pre-marked sensor positions in the heel region (all force sensors the furthest from the middle of the foot). FIGS. 6B and 6C show possible force sensor arrangements on the flexible circuit for medium and large foot pad sizes, respectively, in which force sensors are placed in pre-marked sensor positions intermediate between the small foot pad size of FIG. 6A and the extra large foot pad size of FIG. 6D.

The sensor positions 336 may additionally and/or alternatively include any suitable markings, such as an etched outline, an embossed outline, alignment tick marks, and/or centering tick marks. A force sensor is preferably located on each of a selected portion of the sensor positions for force sensor placement on the flexible circuit, and the selected portion is preferably selected based on foot pad size.

The force sensor connection paths 334 of the flexible circuit 332 are preferably conductive traces formed directly on the flexible circuit 332, but may alternatively be thin wires or any suitable signal conductive paths. At least one force sensor connection path preferably extends from each sensor position 336, such that the force sensor connection path is adapted to transmit force data from a force sensor located at the pre-marked sensor position. In a first variation, the number of force sensor connection paths 334 may be equal to the number of applicable sensor positions 336 such that every force sensor connection path is connected to a force sensor. In a second variation, the number of force sensor connection paths 334 may be greater than the number of applicable sensor positions 336. In this second variation, during construction of the sensor electronics, each of a selected portion of force sensor connection paths may be connected to a force sensor. The selection of connected force sensor connection paths is preferably coupled to the selection of pre-marked sensor positions, which is preferably in turn based on the size of the foot pad. For example, a flexible circuit for a small size foot pad may connect a first subset of the force sensor connection paths to force sensors, whereas a flexible circuit for a large size foot pad may connect a second subset of the force sensor connection paths to force sensors, where the first and second subsets may or may not be mutually exclusive.

Figure 8:
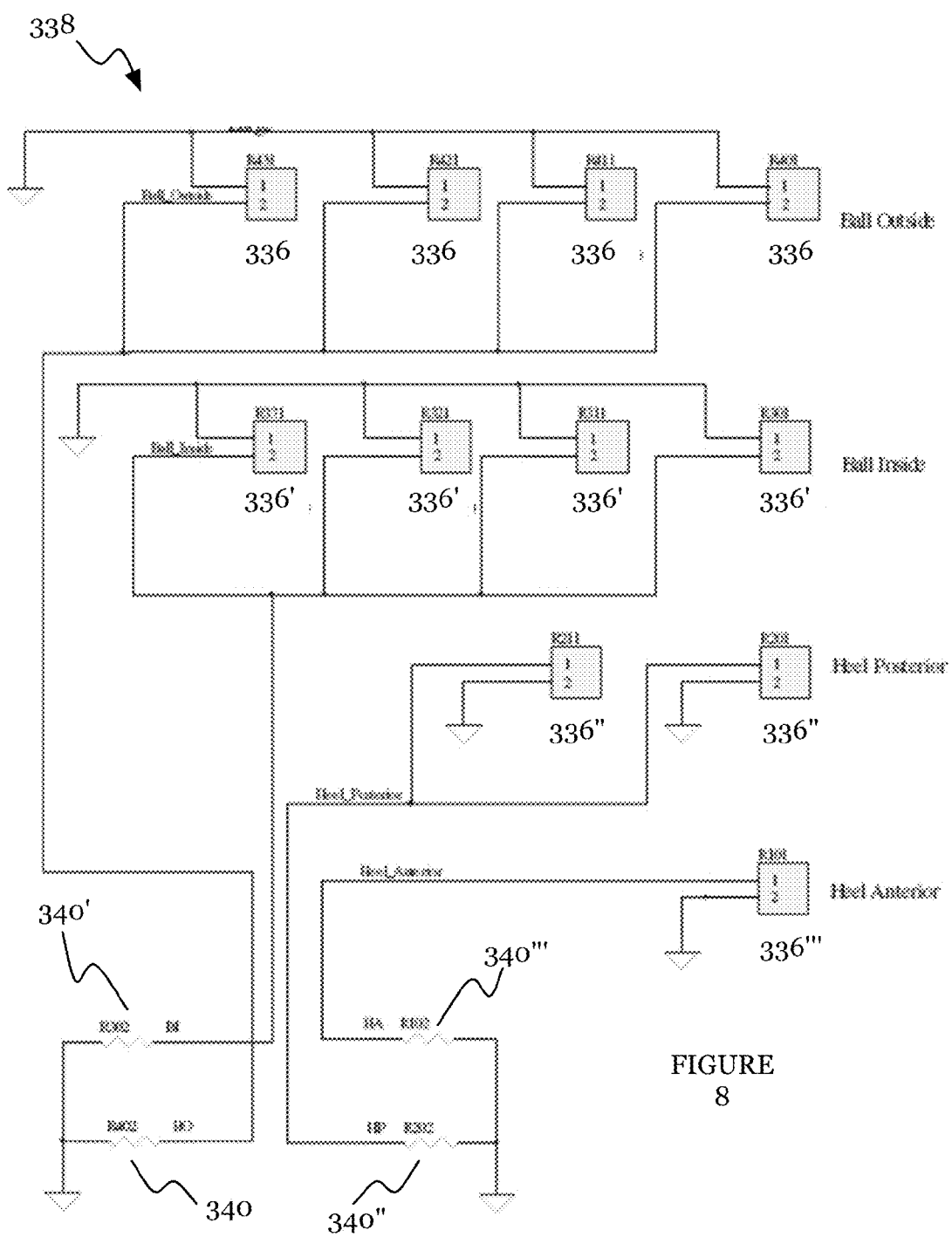
FIG. 8 is a connection schematic of one version of the signal processing circuitry of the foot pad device.

The signal processing circuitry 338 functions to condition the force data from the force sensors. As shown in FIGS. 7 and 8, the signal processing circuitry preferably includes a resistor 340 of a selected value that is electrically connected relative to each connected force sensor connection path and that characterizes the collected force data. The signal processing circuitry may alternatively include a resistor 340 of a selected value that is electrically connected relative to every available force sensor connection path in anticipation of the possibility of being connected to a force sensor, such that a resistor will only have an effect on the force data if it is electrically connected relative to a connected force sensor connection path. As shown in FIG. 8, the resistor 340 is preferably placed in parallel electrically with each force sensor, but may alternatively be placed in any suitable electrical orientation relative to the force sensor connection path and/or force sensor. The resistor value is preferably selected from a set of resistor values, and the resistor value is preferably associated with a foot pad size and/or the selected sensor positions 336, such that the resistor value is selected based on the foot pad size and/or the location of each force sensor. As a result of a set of selected resistor values (one for each connected force sensor connection path), the characterized force data is preferably associated with a foot pad size. The signal processing circuitry may further include analog and/or digital electronics that filter and/or modify the gain value and/or offset value of the force data.

The processor 350 of the foot pad device preferably functions to periodically calculate a weight value based on the conditioned force data. The processor 350 preferably calculates a weight value based on a scaling parameter, which preferably includes a gain value and/or an offset value. For example, the processor preferably calculates a weight value by expressing the calculated weight as a function of the collected force data, the gain value, and the offset value, such as (calculated weight)=(gain)*(collected raw force data)+(offset). The processor 350 preferably analyzes the characterized force data to determine foot pad size. For example, when no weight is applied to a force sensor (which may be recognized by determining phase of the gait cycle of the user using methods similar to the step of receiving information signaling completion of a foot step described above), collected force data from that force sensor is a nominal value that is predictably characterized by the resistor 340. The processor 350 may match the characterized force data to one or more of a set of known characterized force data ranges (for zero weight) that are based on a known set of selectable resistor values, which are each associated with a foot pad size. The processor 350 may then determine the foot pad size by matching the characterized force data to its associated foot pad size. The processor 350 may additionally and/or alternatively include any suitable scaling parameter that scales the conditioned force data. The processor 350 preferably additionally and/or alternatively stores the calculated weight value, adjusts the scaling parameter, and/or analyzes the force data to identify nonfunctional force sensor events, such as by performing method 100 and method 200, as described above. The processor 350 preferably includes analog and/or digital processing elements and firmware.

In one very specific example of the preferred embodiment of the foot pad device, each of four FSR force sensors in the foot pad is preferably pulled up to 3.3V by a nominally 4.75K pullup resistor. The resistance of each FSR ranges from several megaohms with no weight, to approximately 40 ohms with more than 100 lbf. As shown in FIG. 8, each FSR connects between an ADC input of the processor and ground, and acts to pull voltage lower with more applied force to the FSR. Each FSR of the foot pad device generates a voltage that is connected to ADC analog inputs of the processor. The signals connected to the ADC inputs of the processor are designated Foot[3:0] which correspond to four force sensors [HP, BO, HA, BI]. The ADC has a 2.5V reference and all voltages above 2.5V give a maximum value (ox3FF). As shown in FIG. 9, a resistor is placed electrically parallel to a force sensor connection path, which may be connected to an FSR in any one of the pre-marked sensor positions 336 for each FSR area. For example, resistor 340' is placed electrically parallel to the force sensor connection path that may be connected to an FSR in any one of pre-marked sensor positions 336' for a BI force sensor. The parallel resistor 340 placed relative to each connected force sensor connection path preferably has a value of less than 14 Kohms to keep the force sensor voltage data within a predetermined force data range of 0-2.5V. As shown in FIG. 9, two values of resistors 340 are placed parallel to the connected force sensor connection paths depending on the location of the force sensor and foot pad size, with 10K indicating a binary 1 (higher voltage) and 8K indicating a binary 0. The resistors on the four sensors Foot[3:0] provide a 4-bit value that indicates the foot pad size. The processor reads the four sensor values to determine presence or absence of a foot sensor, good or bad sensor connections, and the size of the foot sensor according to the table shown in FIG. 9. The smallest size is size 0, with all sensors closest to the arch, and the largest is size 7 with all sensors farthest from the arch. Some applications may make use of readings from two ball sensors that are in different locations. These nonstandard sizes can be indicated, for instance as size 31 that indicates the ball inside (BI) sensor is farthest from the heel, and the ball outside (BO) sensor is two positions closer to the arch.

As a person skilled in the art will recognize from the previous detailed description and from the figures and claims, modifications and changes can be made to the preferred embodiments of the invention without departing from the scope of this invention defined in the following claims.

We claim:

1. A foot pad device worn on the foot of a user for obtaining weight data comprising:

a foot pad, defining at least one of a ball region located under the ball of the foot of the user and a heel region located under the heel of the foot of the user; wherein the foot pad is selected from a group of foot pads of different sizes;

a plurality of force sensors that provide force data, wherein at least a portion of the plurality of force sensors is located in at least one of the ball region and the heel region;

sensor electronics, coupled to the plurality of force sensors, that condition the force data to be within a conditioned force data range; wherein the sensor electronics include a flexible circuit with a plurality of force sensor connection paths adapted to transmit force data from the plurality of force sensors and defining a plurality of applicable sensor positions; wherein the plurality of force sensors are located in at least a selected portion of the plurality of applicable sensor positions, and the selected portion of the plurality of applicable sensor positions are selected based on the size of the foot pad; and a processor that calculates a weight value based on the conditioned force data.

2. The foot pad device of claim 1, wherein the sensor electronics include a resistor of a selected value that is connected relative to each connected force sensor connection path; wherein the resistor value characterizes the collected force data.

3. The foot pad device of claim 2, wherein the processor flags the force sensor as nonfunctional if the force data is outside of a functionality indication range and disregards force data from the flagged force sensor.

4. The foot pad device of claim 1, wherein the foot pad is wearable.

5. The foot pad device of claim 1, wherein the food pad is adapted to be integrated into a wearable foot article.

6. The foot pad device of claim 1, wherein the foot pad further comprises surface textiles and at least one strap adapted to interface with a user's foot.

7. The foot pad device of claim 1, wherein the foot pad is invertible.

8. The foot pad device of claim 1, wherein the foot pad comprises an arch region, a toe region, a dorsal region, or an ankle region adapted for placement of a force sensor.

9. The foot pad device of claim 1, wherein the plurality of force sensors are adapted to be movable to different locations on the foot pad.

10. The foot pad device of claim 1, wherein the plurality of force sensors are pressure sensors.

11. The foot pad device of claim 1, wherein the plurality of force sensors are piezoelectric sensors.

12. The foot pad device of claim 1, wherein the plurality of force sensors are capacitive sensors.

13. The foot pad device of claim 1, wherein the plurality of force sensors are voltage sensors.

14. The foot pad device of claim 1, wherein the processor is configured to calculate a weight value based on a scaling parameter that includes a gain value.

15. The foot pad device of claim 14, wherein the processor is configured to compare the calculated weight value with an entered patient weight in a first comparison, and to compare the calculated weight value to zero in a second comparison, and to adjust the scaling parameter based on the first and second comparisons.

16. The foot pad device of claim 15, wherein the processor is configured to adjust the scaling parameter by decreasing the gain value if the calculated weight value is greater than the entered patient weight value.

17. The foot pad device of claim 15, wherein the processor is configured to calculate multiple weight values during a footstep cycle and adjust the scaling parameter by increasing the gain value if a maximum of the multiple calculated weight values is less than the entered patient weight value.

18. The foot pad device of claim 1, wherein the processor is configured to determine whether each sensor of the plurality of sensors is providing force data within a functionality indication range.

19. The foot pad device of claim 18, wherein the processor is configured to disregard force data from each sensor of the plurality of sensors that provides force data outside of the functionality indication range.

20. The foot pad device of claim 18, wherein the functionality indication range is a voltage range.

21. The foot pad device of claim 18, wherein the functionality indication range is a resistance range.

22. The foot pad device of claim 1, wherein the processor is configured to calculate a weight value based on the conditioned force data, a gain value, and an offset value.

23. The foot pad device of claim 22, wherein the processor is configured to compare the calculated weight value with an entered patient weight in a first comparison, and compare the calculated weight value to zero in a second comparison, and adjust the offset value based on the first and second comparisons.

24. The foot pad device of claim 23, wherein the processor is configured to calculate multiple weight values during a footstep cycle and decrease the offset value if a minimum of the multiple calculated weight values is greater than zero.

25. A foot pad device worn on the foot of a user for obtaining weight data comprising:

a foot pad, defining at least one of a ball region located under the ball of the foot of the user and a heel region located under the heel of the foot of the user; wherein the foot pad is selected from a group of foot pads of different sizes;

a plurality of force sensors that provide force data, wherein at least a portion of the plurality of force sensors is located in at least one of the ball region and the heel region;

sensor electronics, coupled to the plurality of force sensors, that condition the force data to be within a conditioned force data range; wherein the sensor electronics comprises:

a flexible circuit with a plurality of force sensor connection paths adapted to transmit force data from the plurality of force sensors and defining a plurality of applicable sensor positions; wherein the plurality of force sensors are located in at least a selected portion of the plurality of applicable sensor positions; and a resistor of a selected value that is connected relative to each connected force sensor connection path, wherein the resistor value characterizes the collected force data and the resistor value is associated with the size of the foot pad; and a processor that calculates a weight value based on the conditioned force data.

26. The foot pad device of claim 25, wherein the processor identifies the foot pad size by analyzing the characterized force data.

* * * * *